United States Patent
Sharma et al.

(10) Patent No.: US 10,803,995 B2
(45) Date of Patent: Oct. 13, 2020

(54) METHOD AND SYSTEM FOR NON-INVASIVE FUNCTIONAL ASSESSMENT OF CORONARY ARTERY STENOSIS USING FLOW COMPUTATIONS IN DISEASED AND HYPOTHETICAL NORMAL ANATOMICAL MODELS

(71) Applicant: Siemens Healthcare GmbH, Erlangen (DE)

(72) Inventors: Puneet Sharma, Monmouth Junction, NJ (US); Lucian Mihai Itu, Brasov (RO)

(73) Assignee: Siemens Healthcare GmbH, Erlangen (DE)

(*) Notice: Subject to any disclaimer, the term of this patent is extended or adjusted under 35 U.S.C. 154(b) by 197 days.

(21) Appl. No.: 15/308,825

(22) PCT Filed: Apr. 15, 2015

(86) PCT No.: PCT/US2015/025853
§ 371 (c)(1),
(2) Date: Nov. 3, 2016

(87) PCT Pub. No.: WO2015/171276
PCT Pub. Date: Nov. 12, 2015

(65) Prior Publication Data
US 2017/0068797 A1 Mar. 9, 2017

Related U.S. Application Data

(60) Provisional application No. 61/988,494, filed on May 5, 2014.

(51) Int. Cl.
G16H 50/50 (2018.01)
A61B 5/02 (2006.01)
(Continued)

(52) U.S. Cl.
CPC ......... G16H 50/50 (2018.01); A61B 5/02007 (2013.01); A61B 5/0263 (2013.01);
(Continued)

(58) Field of Classification Search
CPC ........... G06F 17/50; G06T 2207/30048; G06T 2207/30101; G06T 2207/30104; G16H 50/50; A61B 6/504; A61B 5/02007
See application file for complete search history.

(56) References Cited

U.S. PATENT DOCUMENTS 4,692,864 A * 9/1987 Shimoni ............... A61B 6/481
348/E5.089
8,249,815 B2 8/2012 Taylor
(Continued)

FOREIGN PATENT DOCUMENTS

CA 2807586 A1 2/2012
CN 103270513 A 8/2013
(Continued)

OTHER PUBLICATIONS

J. Zhang et al., "Area stenosis associated with non-invasive fractional flow reserve obtained from coronary CT images," 2013 35th Annual International Conference of the IEEE Engineering in Medicine and Biology Society (EMBC), Osaka, 2013, pp. 3865-3868. (Year: 2013).*
(Continued)

*Primary Examiner* — Omar F Fernandez Rivas
*Assistant Examiner* — David A Hopkins

(57) ABSTRACT

A method and system for non-invasive assessment of coronary artery stenosis is disclosed. A patient-specific real anatomical model of a diseased coronary artery of a patient is generated from medical image data of the patient. A hypothetical normal anatomical model is generated for the diseased coronary artery of the patient. Blood flow is simu- (Continued)

lated in each of the patient-specific real anatomical model of the diseased coronary and the hypothetical normal anatomical model for the diseased coronary artery. A hemodynamic index is calculated using simulated blood flow rates in the patient-specific real anatomical model of the diseased coronary and the hypothetical normal anatomical model for the diseased coronary artery. In particular, fractional flow reserve (FFR) for the diseased coronary artery is calculated as the ratio of the simulated blood flow rate in the patient-specific real anatomical model of the diseased coronary artery and the simulated blood flow rate in the hypothetical normal anatomical model for the diseased coronary artery.

21 Claims, 6 Drawing Sheets

(51) Int. Cl.
  *A61B 6/00* (2006.01)
  *A61B 5/026* (2006.01)
  *A61B 8/06* (2006.01)
  *A61B 8/08* (2006.01)
  *A61B 5/021* (2006.01)
  *A61B 5/055* (2006.01)
  *A61B 5/024* (2006.01)
  *A61B 6/03* (2006.01)

(52) U.S. Cl.
  CPC .............. *A61B 6/504* (2013.01); *A61B 6/507* (2013.01); *A61B 6/5217* (2013.01); *A61B 8/06* (2013.01); *A61B 8/5223* (2013.01); *A61B 5/021* (2013.01); *A61B 5/024* (2013.01); *A61B 5/055* (2013.01); *A61B 6/032* (2013.01); *A61B 2576/023* (2013.01)

(56) References Cited

U.S. PATENT DOCUMENTS

| | | | |
|---|---|---|---|
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 8,386,188 B2 | 2/2013 | Taylor et al. | |
| 8,496,594 B2 | 7/2013 | Taylor et al. | |
| 8,523,779 B2 | 9/2013 | Taylor et al. | |
| 8,594,950 B2 | 11/2013 | Taylor | |
| 8,606,530 B2 | 12/2013 | Taylor | |
| 8,630,812 B2 | 1/2014 | Taylor | |
| 9,087,147 B1* | 7/2015 | Fonte ................... A61B 5/7275 | |
| 9,891,044 B2* | 2/2018 | Tu ......................... G01B 21/00 | |
| 2003/0171894 A1* | 9/2003 | Giovanni Battista Mancini ......... A61B 5/02007 | |
| | | | 702/182 |
| 2006/0050941 A1* | 3/2006 | Middleton ............. A61B 6/504 | |
| | | | 382/128 |
| 2010/0021025 A1* | 1/2010 | Hof ....................... G06T 7/0012 | |
| | | | 382/128 |
| 2011/0224542 A1* | 9/2011 | Mittal ................... G06T 7/0016 | |
| | | | 600/425 |
| 2011/0282586 A1* | 11/2011 | Kassab ............... A61B 5/02007 | |
| | | | 702/19 |
| 2012/0041318 A1 | 2/2012 | Taylor | |
| 2012/0041319 A1 | 2/2012 | Taylor et al. | |
| 2012/0041320 A1 | 2/2012 | Taylor | |
| 2012/0041321 A1 | 2/2012 | Taylor et al. | |
| 2012/0041322 A1 | 2/2012 | Taylor et al. | |
| 2012/0041323 A1 | 2/2012 | Taylor et al. | |
| 2012/0041324 A1 | 2/2012 | Taylor et al. | |
| 2012/0041739 A1 | 2/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0072190 A1 | 3/2012 | Sharma et al. | |
| 2012/0150516 A1 | 6/2012 | Taylor et al. | |
| 2013/0013278 A1* | 1/2013 | Hu ........................ G06T 7/0016 | |
| | | | 703/11 |
| 2013/0054214 A1 | 2/2013 | Taylor | |
| 2013/0064438 A1 | 3/2013 | Taylor et al. | |
| 2013/0066618 A1 | 3/2013 | Taylor et al. | |
| 2013/0151163 A1 | 6/2013 | Taylor et al. | |
| 2013/0211728 A1 | 8/2013 | Taylor et al. | |
| 2014/0058715 A1 | 2/2014 | Sharma et al. | |
| 2014/0107935 A1 | 4/2014 | Taylor | |
| 2014/0243662 A1* | 8/2014 | Mittal ..................... A61B 6/481 | |
| | | | 600/425 |
| 2015/0065846 A1* | 3/2015 | Choi .................. A61B 5/02007 | |
| | | | 600/407 |
| 2015/0265162 A1* | 9/2015 | Lavi ..................... A61B 6/5217 | |
| | | | 600/408 |
| 2015/0297373 A1* | 10/2015 | Schmitt ................ A61B 5/0066 | |
| | | | 623/1.16 |
| 2015/0339847 A1* | 11/2015 | Benishti ................. G16H 30/20 | |
| | | | 382/131 |
| 2016/0022371 A1* | 1/2016 | Sauer ..................... A61B 6/504 | |
| | | | 600/407 |

FOREIGN PATENT DOCUMENTS

| | | | |
|---|---|---|---|
| EP | 2538361 A2 | 12/2012 | |
| EP | 2538362 A2 | 12/2012 | |
| EP | 2538361 A3 | 4/2013 | |
| EP | 2538362 A3 | 4/2013 | |
| WO | 2012021307 A2 | 2/2012 | |
| WO | 2014064702 | 5/2014 | |

OTHER PUBLICATIONS

Boogers, Mark J., et al. "Automated quantification of stenosis severity on 64-slice CT: a comparison with quantitative coronary angiography." JACC: Cardiovascular Imaging 3.7 (2010): 699-709. (Year: 2010).*

De Graaf, Michiel A., et al. "Automated quantitative coronary computed tomography correlates of myocardial ischaemia on gated myocardial perfusion SPECT." European journal of nuclear medicine and molecular imaging 40.8 (2013): 1171-1180. (Year: 2013).*

Ryou, Hong Sun, et al. "Construction of healthy arteries using computed tomography and virtual histology intravascular ultrasound." Journal of biomechanics 45.9 (2012): 1612-1618. (Year: 2012).*

VanBavel, E., and J. A. Spaan. "Branching patterns in the porcine coronary arterial tree. Estimation of flow heterogeneity." Circulation research 71.5 (1992): 1200-1212. (Year: 1992).*

Kassab, Ghassan S., et al. "A novel system for the reconstruction of a coronary artery lumen profile in real time: a preclinical validation." American Journal of Physiology—Heart and Circulatory Physiology 297.1 (2009): H485-H492. (Year: 2009).*

Mittal, N., et al. "A computer reconstruction of the entire coronary arterial tree based on detailed morphometric data." Annals of biomedical engineering 33.8 (2005): 1015-1026. (Year: 2005).*

Huo, Yunlong, et al. "A validated predictive model of coronary fractional flow reserve." Journal of the Royal Society Interface 9.71 (2012): 1325-1338. (Year: 2012).*

Yaeger IA. Practicability of Multi-Artery Fractional Flow Reserve (FFR) Method in the Assessment of Some Stenotic Coronary Artery Configurations in Percutaneous Coronary Intervention (PCI) Procedures. Intery Cardiol J 2015,2:3. doi: 10.21767/2471-8157. 100040 (Year: 2016).*

Yaeger, Ilan A. "A multi-artery Fractional Flow Reserve (FFR) approach for handling coronary stenosis-stenosis interaction in the multi-vessel disease (MVD) arena." International journal of cardiology 203 (2016): 807-815. (Year: 2015).*

(56) References Cited

OTHER PUBLICATIONS

Beton, Osman, et al. "Anatomic assessment of the left main bifurcation and dynamic bifurcation angles using computed tomography angiography." Folia morphologica 76.2 (2017): 197-207. (Year: 2017).*

Schindler, Thomas H., et al. "Fusion imaging: combined visualization of 3D reconstructed coronary artery tree and 3D myocardial scintigraphic image in coronary artery disease." The International Journal of Cardiac Imaging 15.5 (1999): 357-368. (Year: 1999).*

Timmins, Lucas H., et al. "Mechanical modeling of stents deployed in tapered arteries." Annals of biomedical engineering 36.12 (2008): 2042-2050. (Year: 2008).*

Taylor, Allen J., et al. "Arterial remodeling in the left coronary system: the role of high-density lipoprotein cholesterol." Journal of the American College of Cardiology 34.3 (1999): 760-767. (Year: 1999).*

Zijlstra, F. E. L. I. X., et al. "Does the quantitative assessment of coronary artery dimensions predict the physiologic significance of a coronary stenosis?." Circulation 75.6 (1987): 1154-1161. (Year: 1987).*

Waksman, Ron, and John A. Ormiston, eds. Bifurcation stenting. Wiley-Blackwell, 2012. Chapter 12 (Year: 2012).*

Dawson, Christopher A., et al. "Structure-function relationships in the pulmonary arterial tree." Journal of Applied Physiology 86.2 (1999): 569-583. (Year: 1999).*

McCulloh, Katherine. Do plants obey Murray's law?. The University of Utah, 2004. PhD Dissertation (Year: 2004).*

Krenz, Gary S., John H. Linehan, and Christopher A. Dawson. "A fractal continuum model of the pulmonary arterial tree." Journal of Applied Physiology 72.6 (1992): 2225-2237. (Year: 1992).*

E. Shalman, et al. "Numerical modeling of the flow in stenosed coronary artery. The relationship between main hemodynamic parameters", Computers in Biology and Medicine, vol. 32, No. 5, Sep. 1, 2002, pp. 329-344.

CN.H. Pijls, B. Bruyne, Coronary Pressure, Springer, Feb. 29, 2000.

Siogkas P. et al. "Computational Assessment of the Fractional Flow Reserve from Intravascular Ultrasound and Coronary Angiography Data: a Pilot Study"; 35th Annual International Conference of the IEEE EMBS; Osaka, Japan, Jul. 3-7, 2013; pp. 3885-3888.

Morris et al., "Virtual Fractional Flow Reserve from Coronary Angiography: Modeling the Significance of Coronary Lesions", J Am Coll Cardiol Intv, vol. 6, pp. 149-157, 2013.

Unkown; "Ultrasound-identified diagnosis of peripheral blood vessels and superficial organs"; Chinese textbook; Jan. 2007.

* cited by examiner

METHOD AND SYSTEM FOR NON-INVASIVE FUNCTIONAL ASSESSMENT OF CORONARY ARTERY STENOSIS USING FLOW COMPUTATIONS IN DISEASED AND HYPOTHETICAL NORMAL ANATOMICAL MODELS

This application claims the benefit of U.S. Provisional Application No. 61/988,494, filed May 4, 2014, the disclosure of which is herein incorporated by reference.

BACKGROUND OF THE INVENTION

The present invention relates to non-invasive functional assessment of coronary artery stenosis, and more particularly, to non-invasive functional assessment of coronary artery stenosis from medical image data and blood flow simulations.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance of the stenosis and has a number of other limitations. Pressure wire based FFR measurements involve risks associated with the intervention necessary to insert the pressure wire into the vessel, and for a very narrow stenosis, the pressure wire may induce an additional pressure drop.

BRIEF SUMMARY OF THE INVENTION

The present invention provides a method and system for non-invasive functional assessment of coronary artery stenosis. Embodiments of the present invention perform medical image based flow computations in diseased and hypothetical normal anatomical models for relative severity assessment.

In one embodiment of the present invention, a patient-specific real anatomical model of a diseased coronary artery of a patient is generated from medical image data of the patient. A hypothetical normal anatomical model is generated for the diseased coronary artery of the patient. Blood flow is simulated in each of the patient-specific real anatomical model of the diseased coronary and the hypothetical normal anatomical model for the diseased coronary artery. A hemodynamic index is calculated using a simulated blood flow rate in the patient-specific real anatomical model of the diseased coronary and a simulated blood flow rate in the hypothetical normal anatomical model for the diseased coronary artery.

These and other advantages of the invention will be apparent to those of ordinary skill in the art by reference to the following detailed description and the accompanying drawings.

DETAILED DESCRIPTION

The present invention relates to a method and system for non-invasive functional assessment of coronary artery stenosis using medical image data and blood flow simulations. Embodiments of the present invention are described herein to give a visual understanding of the methods for simulating blood flow and assessing coronary artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Fractional Flow Reserve (FFR) is a functional measure for quantifying the hemodynamic significance of a coronary stenosis. FFR is typically invasively determined using pressure wire based measurements. FFR is defined as the fraction of the blood flow in the diseased vessel (vessel with stenosis or blockage) to the flow in the same, hypothetical, normal (healthy) vessel, both of which are determined at maximal hyperemia:

$$FFR = \frac{\text{Flow in Stenosed Vessel at maximal hyperemia}}{\text{Flow in hypothetical normal Vessel at maximal hyperemia}} \quad (1)$$

$$FFR = \frac{Q_{max}^{Stenosis}}{Q_{max}^{Normal}}$$

Figure 1:
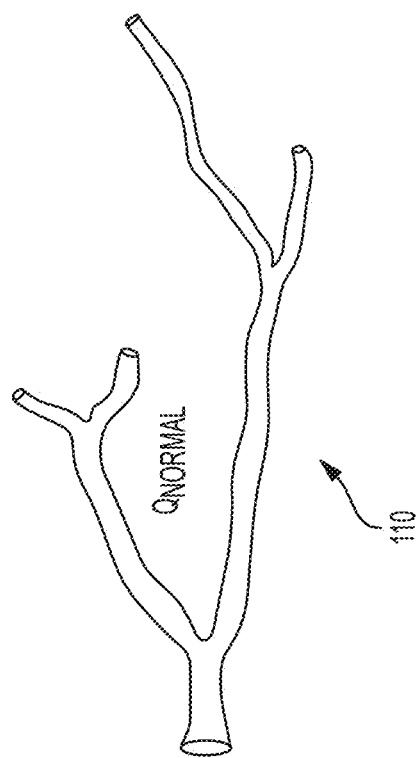
FIG. 1 illustrates a stenosed vessel and a corresponding hypothetical normal vessel.
Figure 1:
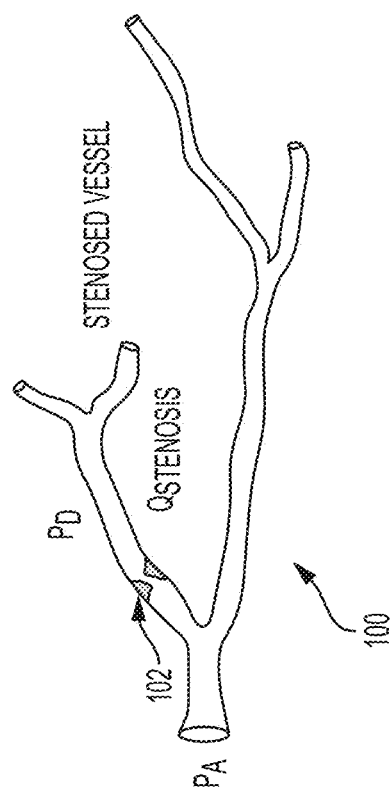

Here, 'max' refers to the maximal hyperemia condition. The normal vessel is hypothetical (i.e., how the vessel would have been if the blockage(s) were not present). Since such a hypothetical normal vessel is not available for measurements, an alternate pressure-based formulation is generally used for quantifying FFR. FIG. 1 illustrates a stenosed vessel 100 and a corresponding hypothetical normal vessel 110. As shown in FIG. 1, a stenosis 102 is present in the stenosed vessel 100, but not in the hypothetical normal vessel 110. $Q_{stenosis}$ refers to the blood flow in the stenosed vessel 100 and $Q_{normal}$ refers to the blood flow in the hypothetical normal vessel 110.

In order to use the alternate pressure-based formulation, it is essential to measure the pressure at maximal hyperemia, when the myocardial resistance is fixed at its lowest value (the pressure and flow variability in a non-maximal hyperemia state may be considerable and hence affect the FFR computation). As a result, flow-rate terms can be substituted by appropriate perfusion pressure terms, all of which can be measured in the stenosed vessel:

$$FFR = \frac{Q_{max}^{Stenosis}}{Q_{max}^{Normal}} = \frac{\Delta P^{Stenosis}}{\Delta P^{Normal}} = \frac{P_d - P_v}{P_a - P_v}. \quad (2)$$

Here, $P_d$ and $P_a$ are average (over the cardiac cycle) distal and aortic pressure, respectively, during hyperemia, and $P_v$ is the venous pressure (which is sometimes assumed to be zero; $P_v \approx 0$).

In recent years, several methods have been proposed for non-invasive computation of FFR (as opposed to using invasive measurements) by utilizing a medical image-based method in conjunction with Computational Fluid Dynamics (CFD) based algorithms. Such methods compute the flow and pressure under a simulated hyperemic state in an anatomical model generated from patient-specific medical image data, and compute the ratio of the time-averaged pressure distal to the stenosis with respect to the average pressure in the aorta to evaluate FFR. One common feature of all such models is the use of the pressure-based formulation to compute FFR.

However, vasodilator agents used to induce hyperemia do not always repeatedly bring down the resistance of the myocardium to the same level. In addition, every vasodilator agent does not produce the exact same reduction in resistance. Further, an elevated venous pressure may invalidate the assumption that the venous pressure is nearly zero, thereby requiring a more sophisticated computation of FFR than the pressure-based formulation to determine an accurate FFR value.

To overcome the limitations of the pressure-based computational approaches for computing FFR, embodiments of the present invention provide a method for non-invasive FFR computation from medical images of a patient based on the flow based formulation of FFR. Embodiments of the present invention generate an anatomical model of the patient's coronary from medical images (referred to as the "real anatomical model"), generate an anatomical model of a hypothetical normal vessel for the patient, perform blood flow simulations in both the real anatomical model and the anatomical model of the hypothetical normal vessel, and compute FFR by calculating the ratio of the simulated flows in the real anatomical model and the anatomical model of the hypothetical vessel. For determining FFR, the flow computations may be performed under hyperemic conditions. Embodiments of the present invention can be similarly applied to compute other hemodynamic indices, and for other hemodynamic indices the flow computations may be performed at rest or at other physiological states of the patient.

Figure 2:
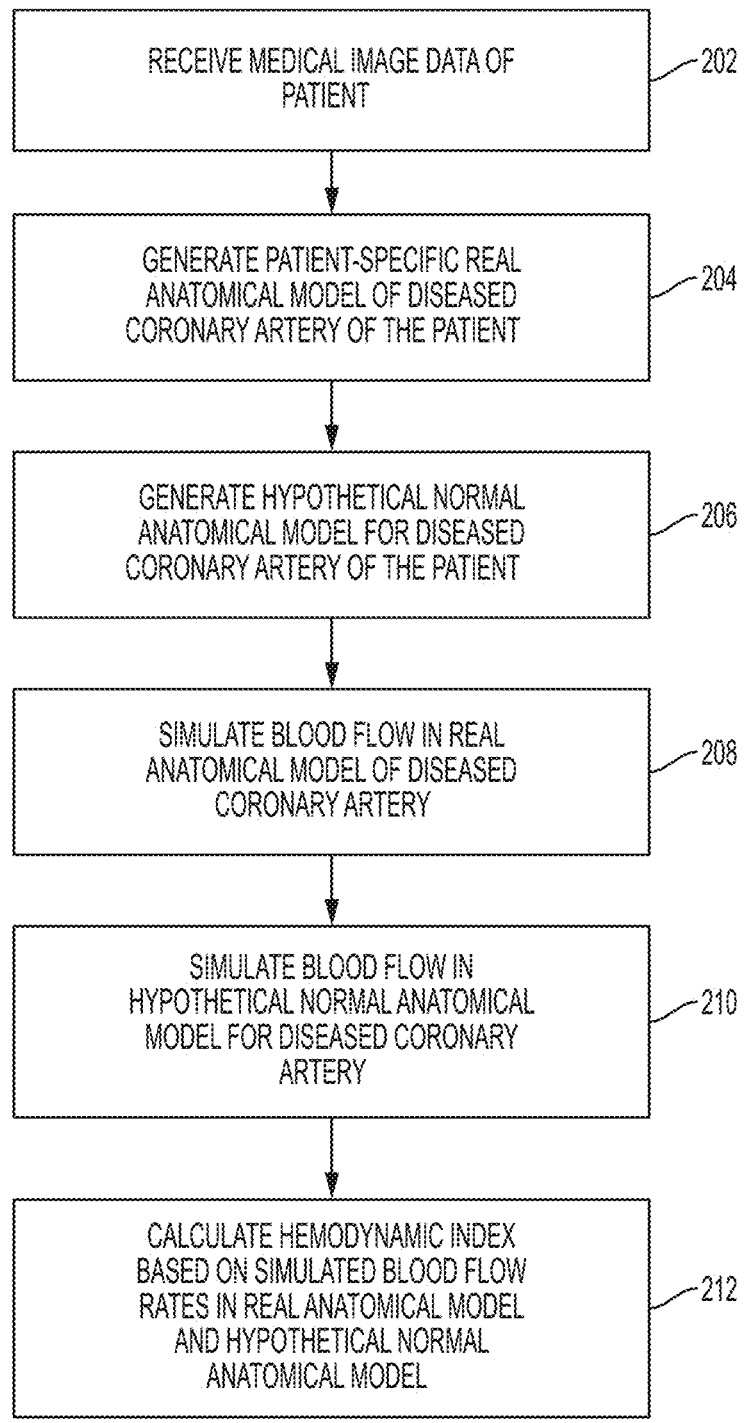
FIG. 2 illustrates a method of non-invasive functional assessment of a coronary artery stenosis according to an embodiment of the present invention.

FIG. 2 illustrates a method of non-invasive functional assessment of a coronary artery stenosis according to an embodiment of the present invention. Referring to FIG. 2, at step 202, medical image data from a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on the patient-specific anatomical model that is extracted from the image data (step 204). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure may also be acquired.

Figure 3:
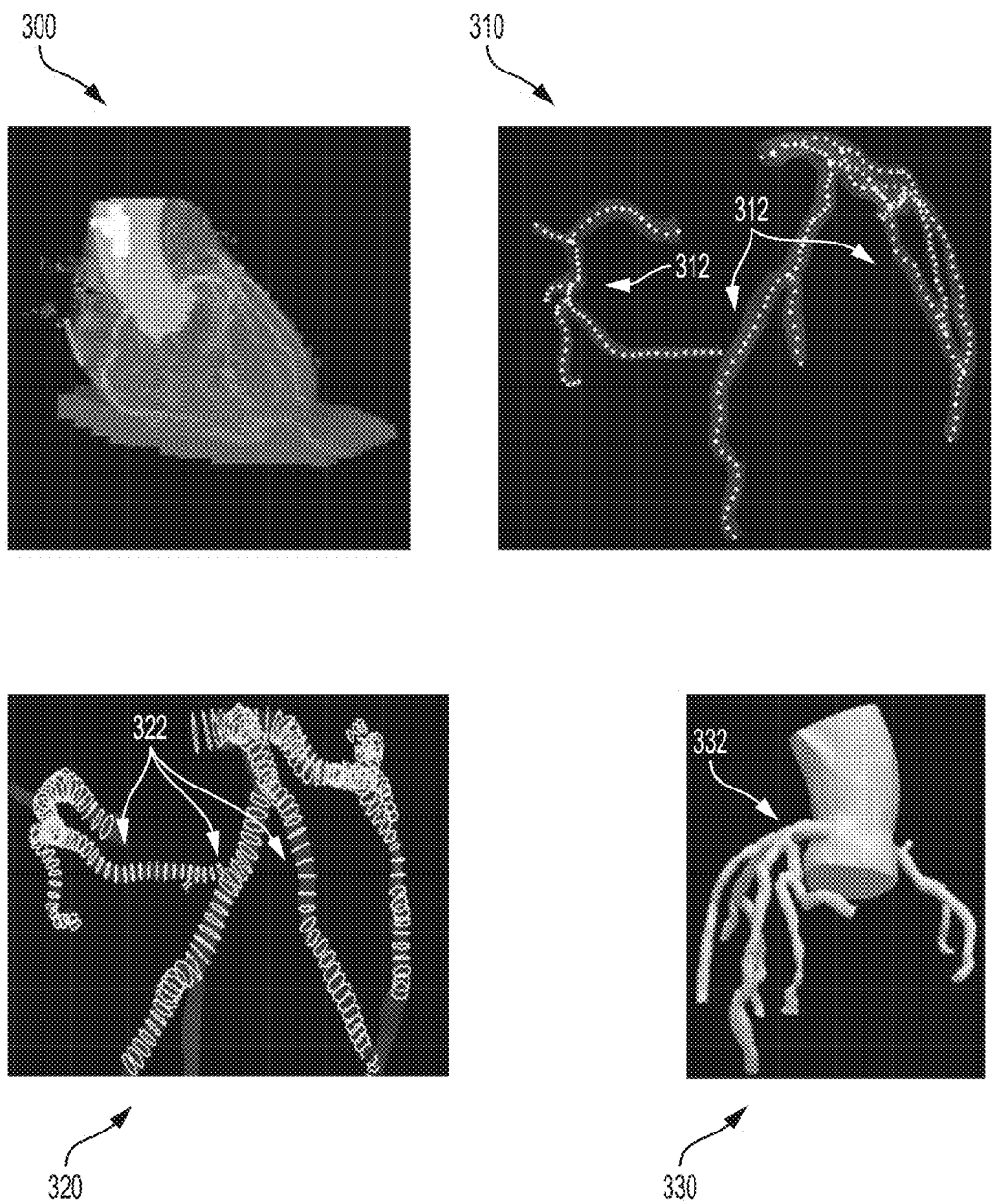
FIG. 3 illustrates exemplary results for generating a patient-specific anatomical model of the coronary vessel tree.

At step 204, a patient-specific real anatomical model of at least one diseased coronary artery of the patient is generated from the medical imaging data of the patient. As used herein, the "real" anatomical model refers to an anatomical model of the patient's actual coronary artery including any stenosis in the coronary artery. A diseased coronary artery is a coronary artery that contains at least one stenosis. In an exemplary embodiment, a patient-specific anatomical model of the patient's coronary artery tree is generated from the medical image data. In order to generate the patient-specific anatomical model of the patient's coronary artery tree, the coronary arteries can be segmented in the 3D medical image data using an automated coronary artery centerline extraction algorithm. The coronary arteries can be segmented using any coronary artery segmentation method. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. Nos. 7,860,290 and 7,953,266, both of which are incorporated herein by reference. In addition to the coronaries, the patient-specific anatomical model can include the aortic root together with the proximal part of the aorta. A detailed 3D model of each stenosis is also extracted using similar algorithms, which includes the quantification of the proximal vessel diameter and area, distal vessel diameter and area, minimal lumen diameter and area, and length of stenosis. FIG. 3 illustrates exemplary results for generating a patient-specific anatomical model of the coronary vessel tree. Image 300 of FIG. 3 shows coronary CTA data. Image 310 shows a centerline tree 312 extracted from the CTA data.

Image 320 shows cross-section contours 322 extracted at each point of the centerline tree 312. Image 330 shows a 3D surface mesh 332 of the coronary arteries, the aortic root, and the proximal part of the aorta. It is to be understood that the real anatomical model of the diseased coronary and/or the entire coronary tree of the patient can be output and displayed, for example on a display screen of the computer system.

Returning to FIG. 2, at step 206, a hypothetical normal anatomical model for the at least one diseased coronary artery is generated. As used herein, the hypothetical normal anatomical model is an anatomical model representing the diseased coronary artery in a hypothetical normal or healthy state without the stenosis. Since such a hypothetical normal vessel is not present in the medical image data of the patient, various embodiments of the present invention are described herein that utilize different techniques for generating the hypothetical normal anatomical model of a diseased coronary artery. It is to be understood that the hypothetical normal anatomical model for the diseased coronary and/or a hypothetical normal anatomical model for the entire coronary tree of the patient can be output and displayed, for example on a display screen of the computer system.

Figure 4:
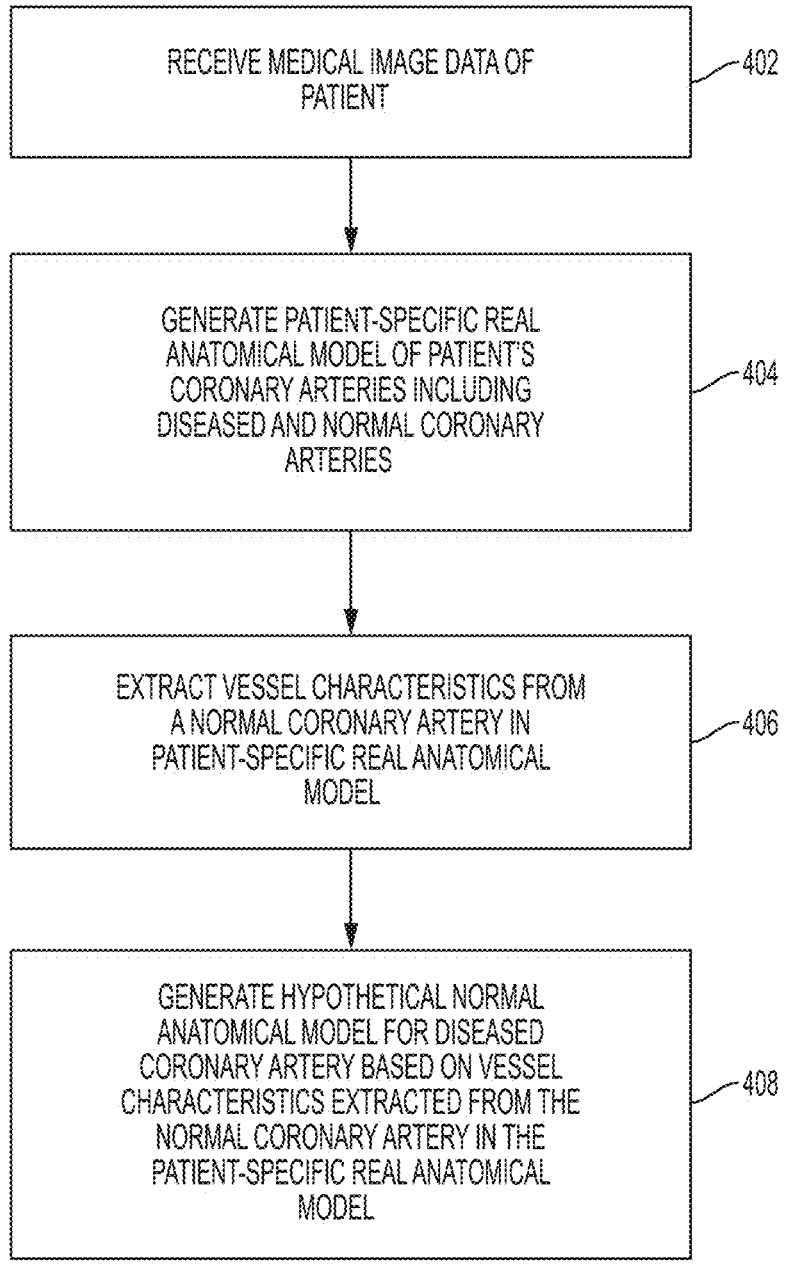
FIG. 4 illustrates a method for generating a hypothetical normal anatomical model for a diseased coronary artery according to an embodiment of the present invention.

FIG. 4 illustrates a method for generating a hypothetical normal anatomical model for a diseased coronary artery according to an embodiment of the present invention. In the embodiment of FIG. 4, the hypothetical normal anatomical model is generated by analyzing a real normal (healthy) vessel from the patient's coronary artery tree, computing anatomical characteristics from the real normal vessel and using these characteristics to synthesize the hypothetical normal anatomical model of the diseased vessel. As illustrated in FIG. 4, at step 402, medical image data of the patient is received. Step 402 of FIG. 4 is similar to step 202 of FIG. 2. At step 404 of FIG. 4, a patient-specific real anatomical model of the patient's coronary arteries including the diseased coronary artery an at least one normal (healthy) coronary artery is generated from the medical imaging data of the patient. For example, the patient-specific real anatomical model of the patient's coronary arteries including the diseased coronary artery and at least one healthy coronary artery can be generated by generating a patient-specific anatomical model of the patient's coronary tree as described above in connection with step 204 of FIG. 2.

At step 406, vessel characteristics are extracted from a normal coronary artery in the patient-specific real anatomical model of the patient's coronary arteries. First, the normal coronary artery must be determined by finding a healthy branch of the coronary tree. In one possible implementation, the normal coronary artery can be determined by receiving an input selection of a normal coronary artery from a user. In another possible implementation, the normal coronary artery can be determined by automatically detecting a healthy coronary artery in the medical image data or in the patient-specific real anatomical model of the patient's coronary arteries. For example, a method for automatic detection of coronary artery stenoses, such as the method described in United States Published Patent Application No. 2011/0224542, which is incorporated herein by reference, may be performed on the medical image data or the patient-specific real anatomical model, and a coronary artery in which no stenosis was detected can be automatically selected as a normal coronary artery. Once the normal coronary artery is determined, vessel characteristics are extracted from the normal coronary artery in the patient-specific real anatomical model. In an advantageous embodiment, the radius of the normal coronary artery is extracted over the length of the normal coronary artery and rate of change of the radius over the length of the coronary artery is determined.

At step 408, the hypothetical normal anatomical model for the diseased coronary artery is generated based on the vessel characteristics extracted from the normal coronary artery in the patient-specific real anatomical model. In an advantageous embodiment, the hypothetical normal anatomical model has the same length as the diseased coronary artery in the patient-specific real anatomical model and the same radius as the diseased coronary artery in non-diseased portions of the diseased coronary artery. The radius of the hypothetical normal anatomical model in the diseased (e.g., stenosis) portions of the diseased coronary artery is determined by applying the rate of change of the radius extracted from the normal coronary artery. For example, consider a patient with a stenosis and calcification in the left anterior descending (LAD) artery, with a normal left circumflex (LCX) artery. In order to generate a hypothetical anatomical model of the LAD artery, the rate of change of radius in the patient's normal LCX artery can be extracted and this information can then be used to generate the hypothetical normal anatomical model of the LAD artery. This synthetically generated hypothetical normal anatomical model of the LAD artery may have the same length as the original diseased LAD, but a different cross-sectional profile.

Figure 5:
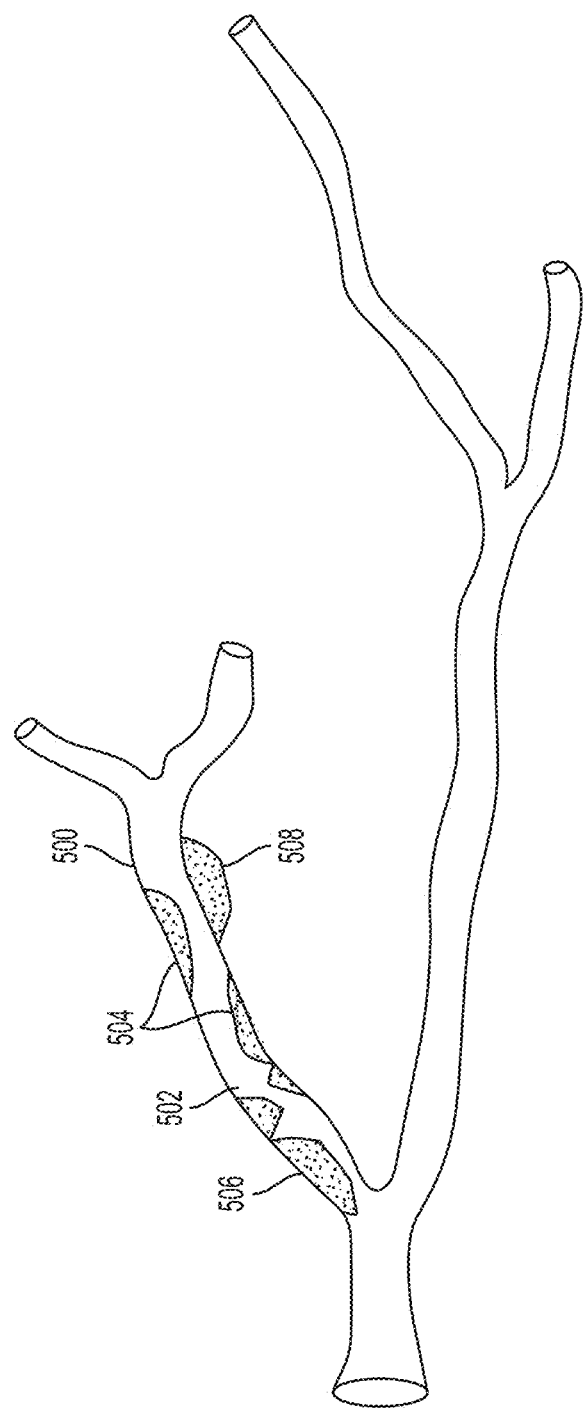
FIG. 5 illustrates a diseased coronary artery with diseased portions highlighted.

In another embodiment, the hypothetical normal anatomical model for the diseased coronary artery may be generated by modifying the patient-specific real anatomical model of the diseased coronary artery or the underlying medical image of the diseased vessel based on user input. This may be performed by removing certain characteristics such as, but not limited to, plaque, calcification, thrombus, stenosis or other vessel narrowing, and positive remodeling. These characteristics may be highlighted on the medical image or on the real anatomical model of the diseased coronary artery, and then removed either automatically or based on a user's input to create the hypothetical normal anatomical model for the diseased vessel. In this embodiment, the medical image and/or the patient-specific real anatomical model can be displayed, for example on a display screen of a computer system, and the user input can be received by the user highlighting portions to be removed on the displayed medical image or real anatomical model using an input device, such as a mouse, touchscreen, etc. FIG. 5 illustrates a diseased coronary artery with diseased portions highlighted. As shown in FIG. 5, stenosis/plaque 502, calcifications 504, thrombus 506, and positive remodeling 508 are highlighted on the diseased coronary artery 500.

In another embodiment, the hypothetical normal anatomical model for the diseased coronary artery can be generated based on the patient-specific real anatomical model of the diseased coronary artery by replacing diseased (e.g., stenosis) segments of the diseased coronary artery with normal segments that are either proximal or distal to the diseased segments. In this embodiment, each diseased segment of the diseased coronary artery is replaced by interpolating the vessel geometry of normal segment that is proximal or distal to the diseased segment over the length of the diseased segment.

In another embodiment, the hypothetical normal anatomical model for the diseased coronary artery may be generated in the medical image itself, either during the image reconstruction stage or during the image processing stage. In this embodiment, the hypothetical normal anatomical model can be generated based on fully automatic detection of diseased features such as calcification and stenosis. For example, in the case of computed tomography (CT) images, the Hounsfield units of the image voxels can be used to automatically detect disease features such as calcification and subsequently removed to generate the hypothetical normal anatomical model for the diseased coronary artery. In one implementation, the boundaries of the segmented diseased coronary artery can be automatically modified to remove some or all of the detected diseased features from the segmented diseased coronary artery. In another implementation, the medical image data can be modified to change the voxel intensity values of the voxels detected as the diseased features. For example, the voxels of the detected diseased features can be modified to have voxel values equal to an average intensity of a healthy region of a coronary artery. Once the medical image data is modified, the hypothetical normal anatomical model can be generated by segmenting the coronary artery in the modified medical image.

Returning to FIG. 2, at step 208, blood flow is simulated in the patient-specific real anatomical model of the diseased coronary artery. In an advantageous implementation, the blood flow can be simulated in the patient-specific real anatomical model of the diseased coronary artery of the patient using a Computational Fluid Dynamics (CFD) based algorithm. In CFD based simulation, blood is modeled as a Newtonian fluid, and the velocity field for the blood is obtained by numerically solving the discretized Navier-Stokes equations (continuity and momentum equations) under the rigid wall assumption. The discretized Navier-Stokes equations are used to incrementally simulate velocity of blood flow and pressure within the diseased coronary artery over time. The patient-specific anatomy of the diseased coronary artery from the patient-specific real anatomical model of the diseased coronary artery is also input to the CFD modeling in order to constrain the blood flow simulations based on the patient-specific anatomy. Other boundary conditions, such as velocity and/or pressure boundary conditions are also determined from the medical image data and/or other non-invasive clinical measurements, such as the patient's heart rate and systolic and diastolic blood pressure, acquired for the patient. It is to be understood that the blood flow in the real anatomical model of the diseased coronary artery can be estimated by simulating the blood flow in a real anatomical model of the patient's entire coronary artery tree. For determining FFR, the blood flow simulation may be performed under hyperemic conditions. The boundary conditions representing hyperemic conditions can be determined from the medical image data and/or other non-invasive measurements acquired from the patient at hyperemia, or can be calculated based on rest-state boundary conditions determined from medical image data and/or other non-invasive measurements acquired from the patient at rest. Additional details for various methods that can be used for CFD-based blood flow simulation, including methods for calculating boundary conditions, are described in U.S. Published Patent Application No. 20140058715 and U.S. Published Patent Application No. 2012/0072190, which are incorporated herein by reference in their entirety.

At step 210, blood flow is simulated in the hypothetical normal model for the diseased coronary artery. Similar to the blood flow simulation performed for the patient specific real anatomical model of the diseased coronary artery, the blood flow can be simulated in the hypothetical normal anatomical model for the diseased coronary artery using a Computational Fluid Dynamics (CFD) based algorithm. In the CFD based simulation, blood is modeled as a Newtonian fluid, and the velocity field for the blood is obtained by numerically solving the discretized Navier-Stokes equations (continuity and momentum equations) under the rigid wall assumption. The discretized Navier-Stokes equations are used to incrementally simulate velocity of blood flow and pressure within the hypothetical normal coronary artery over time. The anatomy of the hypothetical normal coronary artery from the hypothetical normal anatomical model for the diseased coronary artery is also input to the CFD modeling workflow in order to constrain the blood flow simulations based on the hypothetical normal anatomy. Other boundary conditions, such as velocity and/or pressure boundary conditions are also determined from the medical image data and/or other non-invasive clinical measurements, such as the patient's heart rate and systolic and diastolic blood pressure, acquired for the patient. It is to be understood that the blood flow in the hypothetical normal anatomical model for the diseased coronary artery can be estimated by simulating the blood flow in a hypothetical normal anatomical model of the patient's entire coronary artery tree. In an alternative implementation, the hypothetical normal coronary artery tree can be used for the estimation of the boundary conditions. Since the computation of parameter values in the boundary conditions is based on the radii of the vessels, the information form the hypothetical normal coronary artery tree may lead to an estimation of flow rate distribution which is closer to the patient-specific values. In this case, boundary conditions for the blood flow simulations in both the real anatomical model of the diseased coronary artery (step 208) and in the hypothetical normal anatomical model for the diseased coronary artery (step 210) may be computed using the hypothetical normal coronary artery tree. For determining FFR, the blood flow simulation may be performed under hyperemic conditions. The boundary conditions representing hyperemic conditions can be determined from the medical image data and/or other non-invasive measurements acquired from the patient at hyperemia, or can be calculated based on rest-state boundary conditions determined from medical image data and/or other non-invasive measurements acquired from the patient at rest. Additional details for various methods that can be used for CFD-based blood flow simulation, including methods for calculating boundary conditions, are described in U.S. Published Patent Application No. 20140058715 and U.S. Published Patent Application No. 2012/0072190, which are incorporated herein by reference in their entirety At step 212, a hemodynamic index is calculated based on the simulated blood flow rate in the patient-specific real anatomical model of the diseased coronary artery and the simulated blood flow rate in the hypothetical normal anatomical model for the diseased coronary artery. In an advantageous embodiment, FFR for the diseased coronary artery is calculated by calculating the ratio of the simulated blood flow rate in the patient-specific real anatomical model of the diseased coronary artery to the simulated blood flow rate in the hypothetical normal anatomical model for the diseased coronary artery. For the FFR computation, the blood flow in both the real anatomical model and the hypothetic normal anatomical model is simulated under hyperemic condition. It is to be understood that, according to an advantageous embodiment of the present invention, the FFR is calculated directly from the simulated flow rates, not from the pressures in the coronary artery. For other hemodynamic indices, the simulations can be performed at a rest state or other physiological states. The simulated flow rates in the real and hypothetical normal anatomical models can be combined in any way to generate a hemodynamic index or metric for assessing the coronary artery stenosis in the diseased coronary artery.

Figure 6:
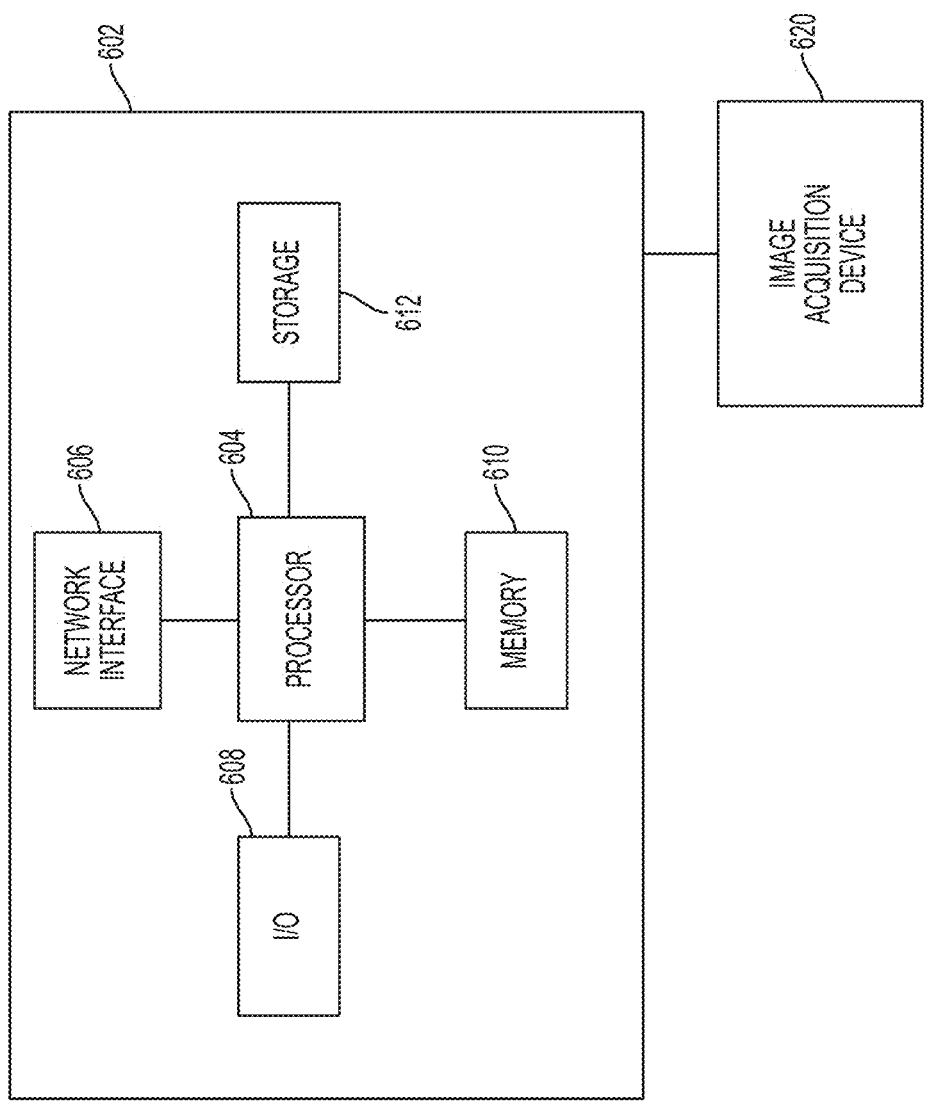
FIG. 6 is a high-level block diagram of a computer capable of implementing the present invention.

The above-described methods for non-invasive assessment of coronary artery stenosis may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIG. 2 and FIG. 4 may be defined by the computer program instructions stored in the memory 610 and/or storage 612 and controlled by the processor 604 executing the computer program instructions. An image acquisition device 620, such as a CT scanning device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasive assessment of coronary artery stenosis, comprising:
    generating a patient-specific real anatomical model of a coronary artery tree of a patient from medical image data of the patient, the coronary artery tree of the patient comprising a diseased coronary artery of the patient and a healthy coronary artery of the patient;
    generating a hypothetical normal anatomical model for the diseased coronary artery of the patient by extracting radius values of the healthy coronary artery from the patient-specific real anatomical model over a length of the healthy coronary artery, determining a rate of change of a radius of the healthy coronary artery over the length based on the extracted radius values, and determining a radius of diseased portions of the diseased coronary artery for the hypothetical normal anatomical model based on the rate of change of the radius of the healthy coronary artery over the length;
    simulating blood flow in each of the patient-specific real anatomical model of the diseased coronary artery and the hypothetical normal anatomical model for the diseased coronary artery; and
    calculating a hemodynamic index using a simulated blood flow rate in the patient-specific real anatomical model of the diseased coronary artery and a simulated blood flow rate in the hypothetical normal anatomical model for the diseased coronary artery.

2. The method of claim 1, wherein generating a hypothetical normal anatomical model for the diseased coronary artery of the patient comprises:
    automatically detecting the healthy coronary artery in one of the patient-specific real anatomical model of the coronary artery tree of the patient or the medical image data of the patient prior to extracting vessel characteristics from the healthy coronary artery.

3. The method of claim 1, wherein generating a hypothetical normal anatomical model for the diseased coronary artery of the patient comprises:
    generating the hypothetical normal anatomical model for the diseased coronary artery such that the hypothetical normal anatomical model for the diseased coronary artery has a length that is the same as a length of the diseased coronary artery in the patient-specific real anatomical model of the coronary artery tree and a radius in healthy regions in the diseased coronary artery that is the same as a radius of the diseased coronary artery in the patient-specific real anatomical model of the coronary artery tree.

4. The method of claim 1, wherein simulating blood flow in each of the patient-specific real anatomical model of the diseased coronary artery and the hypothetical normal anatomical model for the diseased coronary artery comprises:
    simulating blood flow in each of the patient-specific real anatomical model of the diseased coronary artery and the hypothetical normal anatomical model for the diseased coronary artery using respective computational fluid dynamics (CFD) based simulations.

5. The method of claim 1, wherein simulating blood flow in each of the patient-specific real anatomical model of the diseased coronary artery and the hypothetical normal anatomical model for the diseased coronary artery comprises:
    simulating blood flow at hyperemia in each of the patient-specific real anatomical model of the diseased coronary artery and the hypothetical normal anatomical model for the diseased coronary artery using respective computational fluid dynamics (CFD) simulations.

6. The method of claim 1, wherein calculating a hemodynamic index using a simulated blood flow rate in the patient-specific real anatomical model of the diseased coronary artery and a simulated blood flow rate in the hypothetical normal anatomical model for the diseased coronary artery comprises:
    calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery.

7. The method of claim 6, wherein calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery comprises:

calculating FFR for the diseased coronary artery of the patient as a ratio of the simulated blood flow rate in the patient-specific real anatomical model of the diseased coronary artery to the simulated blood flow rate in the hypothetical normal anatomical model for the diseased coronary artery.

8. An apparatus for non-invasive assessment of coronary artery stenosis, comprising:
a processor; and
a memory to store computer program instructions, the computer program instructions when executed on the processor cause the processor to perform operations comprising:
generating a patient-specific real anatomical model of a coronary artery tree of a patient from medical image data of the patient, the coronary artery tree of the patient comprising a diseased coronary artery of the patient and a healthy coronary artery of the patient;
generating a hypothetical normal anatomical model for the diseased coronary artery of the patient by extracting radius values of the healthy coronary artery from the patient-specific real anatomical model over a length of the healthy coronary artery, determining a rate of change of a radius of the healthy coronary artery over the length based on the extracted radius values, and determining a radius of diseased portions of the diseased coronary artery for the hypothetical normal anatomical model based on the rate of change of the radius of the healthy coronary artery over the length;
simulating blood flow in each of the patient-specific real anatomical model of the diseased coronary artery and the hypothetical normal anatomical model for the diseased coronary artery; and
calculating a hemodynamic index using a simulated blood flow rate in the patient-specific real anatomical model of the diseased coronary artery and a simulated blood flow rate in the hypothetical normal anatomical model for the diseased coronary artery.

9. The apparatus of claim 8, wherein generating a hypothetical normal anatomical model for the diseased coronary artery of the patient comprises:
automatically detecting the healthy coronary artery in one of the patient-specific real anatomical model of the coronary artery tree of the patient or the medical image data of the patient.

10. The apparatus of claim 8, wherein generating a hypothetical normal anatomical model for the diseased coronary artery of the patient comprises:
generating the hypothetical normal anatomical model for the diseased coronary artery such that the hypothetical normal anatomical model for the diseased coronary artery has a length that is the same as a length of the diseased coronary artery in the patient-specific real anatomical model of the coronary artery tree and a radius in healthy regions in the diseased coronary artery that is the same as a radius of the diseased coronary artery in the patient-specific real anatomical model of the coronary artery tree.

11. The apparatus of claim 8, wherein simulating blood flow in each of the patient-specific real anatomical model of the diseased coronary artery and the hypothetical normal anatomical model for the diseased coronary artery comprises:
simulating blood flow in each of the patient-specific real anatomical model of the diseased coronary artery and the hypothetical normal anatomical model for the diseased coronary artery using respective computational fluid dynamics (CFD) based simulations.

12. The apparatus of claim 8, wherein simulating blood flow in each of the patient-specific real anatomical model of the diseased coronary artery and the hypothetical normal anatomical model for the diseased coronary artery comprises:
simulating blood flow at hyperemia in each of the patient-specific real anatomical model of the diseased coronary artery and the hypothetical normal anatomical model for the diseased coronary artery using respective computational fluid dynamics (CFD) simulations.

13. The apparatus of claim 8, wherein calculating a hemodynamic index using a simulated blood flow rate in the patient-specific real anatomical model of the diseased coronary artery and a simulated blood flow rate in the hypothetical normal anatomical model for the diseased coronary artery comprises:
calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery.

14. The apparatus of claim 13, wherein calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery comprises:
calculating FFR for the diseased coronary artery of the patient as a ratio of the simulated blood flow rate in the patient-specific real anatomical model of the diseased coronary artery to the simulated blood flow rate in the hypothetical normal anatomical model for the diseased coronary artery.

15. A non-transitory computer readable medium storing computer program instructions for non-invasive assessment of coronary artery stenosis, the computer program instructions when executed by a processor cause the processor to perform operations comprising:
generating a patient-specific real anatomical model of a coronary artery tree of a patient from medical image data of the patient, the coronary artery tree of the patient comprising a diseased coronary artery of the patient and a healthy coronary artery of the patient;
generating a hypothetical normal anatomical model for the diseased coronary artery of the patient by extracting radius values of the healthy coronary artery from the patient-specific real anatomical model over a length of the healthy coronary artery, determining a rate of change of a radius of the healthy coronary artery over the length based on the extracted radius values, and determining a radius of diseased portions of the diseased coronary artery for the hypothetical normal anatomical model based on the rate of change of the radius of the healthy coronary artery over the length;
simulating blood flow in each of the patient-specific real anatomical model of the diseased coronary artery and the hypothetical normal anatomical model for the diseased coronary artery; and
calculating a hemodynamic index using a simulated blood flow rate in the patient-specific real anatomical model of the diseased coronary artery and a simulated blood flow rate in the hypothetical normal anatomical model for the diseased coronary artery.

16. The non-transitory computer readable medium of claim 15, wherein generating a hypothetical normal anatomical model for the diseased coronary artery of the patient comprises:
  automatically detecting the healthy coronary artery in one of the patient-specific real anatomical model of the coronary artery tree of the patient or the medical image data of the patient prior to extracting vessel characteristics from the healthy coronary artery.

17. The non-transitory computer readable medium of claim 15, wherein generating a hypothetical normal anatomical model for the diseased coronary artery of the patient comprises:
  generating the hypothetical normal anatomical model for the diseased coronary artery such that the hypothetical normal anatomical model for the diseased coronary artery has a length that is the same as a length of the diseased coronary artery in the patient-specific real anatomical model of the coronary artery tree and a radius in healthy regions in the diseased coronary artery that is the same as a radius of the diseased coronary artery in the patient-specific real anatomical model of the coronary artery tree.

18. The non-transitory computer readable medium of claim 15, wherein simulating blood flow in each of the patient-specific real anatomical model of the diseased coronary artery and the hypothetical normal anatomical model for the diseased coronary artery comprises:
  simulating blood flow in each of the patient-specific real anatomical model of the diseased coronary artery and the hypothetical normal anatomical model for the diseased coronary artery using respective computational fluid dynamics (CFD) based simulations.

19. The non-transitory computer readable medium of claim 15, wherein simulating blood flow in each of the patient-specific real anatomical model of the diseased coronary artery and the hypothetical normal anatomical model for the diseased coronary artery comprises:
  simulating blood flow at hyperemia in each of the patient-specific real anatomical model of the diseased coronary artery and the hypothetical normal anatomical model for the diseased coronary artery using respective computational fluid dynamics (CFD) simulations.

20. The non-transitory computer readable medium of claim 15, wherein calculating a hemodynamic index using a simulated blood flow rate in the patient-specific real anatomical model of the diseased coronary artery and a simulated blood flow rate in the hypothetical normal anatomical model for the diseased coronary artery comprises:
  calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery.

21. The non-transitory computer readable medium of claim 20, wherein calculating fractional flow reserve (FFR) for the diseased coronary artery of the patient using the simulated blood flow rate in the patient-specific real anatomical model of the diseased coronary artery and the simulated blood flow rate in the hypothetical normal anatomical model for the diseased coronary artery comprises:
  calculating FFR for the diseased coronary artery of the patient as a ratio of the simulated blood flow rate in the patient-specific real anatomical model of the diseased coronary artery to the simulated blood flow rate in the hypothetical normal anatomical model for the diseased coronary artery.

* * * * *